US009187392B2

(12) United States Patent
Li et al.

(10) Patent No.: US 9,187,392 B2
(45) Date of Patent: Nov. 17, 2015

(54) PRODUCTION OF PROPYLENE GLYCOL MONOALKYL ETHER

(75) Inventors: Xiangmin Li, Glen Mills, PA (US); Lawrence M. Candela, Havertown, PA (US); Mark A. Liepa, Exton, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 711 days.

(21) Appl. No.: 12/009,212

(22) Filed: Jan. 17, 2008

(65) Prior Publication Data

US 2009/0187049 A1    Jul. 23, 2009

(51) Int. Cl.
*C07C 41/03* (2006.01)
*C07C 43/13* (2006.01)
*C07C 41/44* (2006.01)

(52) U.S. Cl.
CPC ............. *C07C 41/03* (2013.01); *C07C 41/44* (2013.01)

(58) Field of Classification Search
None
See application file for complete search history.

(56) References Cited

U.S. PATENT DOCUMENTS

| 2,035,383 | A | * | 3/1936 | Cox | 568/582 |
|---|---|---|---|---|---|
| 2,327,053 | A | | 8/1943 | Marple et al. | |
| 3,146,272 | A | * | 8/1964 | Lloyd | 568/582 |
| 3,168,569 | A | * | 2/1965 | Matell | 568/621 |
| 3,205,269 | A | * | 9/1965 | Friedman | 568/581 |
| 3,347,934 | A | * | 10/1967 | Lewis | 568/600 |
| 3,374,275 | A | * | 3/1968 | Dickey | 568/582 |
| 3,972,948 | A | * | 8/1976 | Laemmle et al. | 568/618 |
| 6,235,940 | B1 | * | 5/2001 | Mohr et al. | 564/468 |
| 2004/0211658 | A1 | | 10/2004 | Sanderson et al. | |

FOREIGN PATENT DOCUMENTS

| CN | 1597649 | A | | 3/2005 | |
|---|---|---|---|---|---|
| CN | 1699320 | A | | 11/2005 | |
| CN | 10699320 | A | | 11/2005 | |
| GB | 271169 | | | 5/1927 | |
| GB | 2119373 | A | | 11/1983 | |
| JP | 56015229 | | | 2/1981 | |
| JP | S581968432 | A | | 11/1983 | |
| JP | S61186337 | A | | 8/1986 | |
| JP | S61246140 | A | | 11/1986 | |
| JP | 05-246920 | | * | 9/1993 | ............. C07C 43/10 |
| JP | H05-246920 | | | 9/1993 | |
| JP | H05294880 | A | | 11/1993 | |

OTHER PUBLICATIONS

PCT International Search Report and the Written Opinion—Mailed Jan. 22, 2009 for Corresponding PCT/US2008/012827.
Zhaosheng Jin; A new technological development on the synthesis of propylene glycol ethers, <<Shanghai Chemical Industry>>, vol. 22, No. 3, Jun. 30, 1997, pp. 6-11.

* cited by examiner

*Primary Examiner* — Rosalynd Keys

(57) ABSTRACT

The invention is a process for producing a propylene glycol monoalkyl ether which comprises first reacting propylene oxide and an alcohol in the presence of an alkali or alkaline earth metal alkoxide catalyst to produce an alkoxylation mixture comprising propylene glycol monoalkyl ether; distilling the alkoxylation mixture to produce a first overhead stream comprising propylene oxide and alcohol and a first bottoms stream comprising propylene glycol monoalkyl ether; and then distilling the first bottoms stream to produce purified propylene glycol monoalkyl ether as a second overhead stream. The reaction and/or one or more of the distillation steps occur in the presence of an alkali metal borohydride. The process produces propylene glycol monoalkyl ether with low UV absorbance and reduced carbonyl impurities.

20 Claims, No Drawings

PRODUCTION OF PROPYLENE GLYCOL MONOALKYL ETHER

FIELD OF THE INVENTION

This invention relates to a process for producing a propylene glycol monoalkyl ether.

BACKGROUND OF THE INVENTION

Propylene glycol monoalkyl ethers are high-performance industrial solvents for paints and coatings, cleaners, inks, and a variety of other applications, including agricultural, cosmetic, electronic, textile, and adhesive products. They are also used as chemical intermediates for end-products such as propylene glycol ether acetates.

Typically, propylene glycol monoalkyl ethers are formed by the reaction of propylene oxide with an alcohol, such as methanol or 1-butanol. Although a catalyst is not required, the reaction is typically performed in the presence of a catalyst. A wide variety of catalysts and reaction conditions are taught in the prior art.

The catalysts used in this process include acidic, basic, and neutral species. Particularly useful catalysts include acids such as sulfuric acid, boric acid and some fluorine-containing acids; or bases such as alkali and alkaline earth metal hydroxides and alkoxides, tertiary amines, and certain metal oxides. G.B. Pat. No. 271,169, for instance, discloses the use of sulfuric acid, alkali metal alkoxides, and alkali metal salts of lower fatty acids. U.S. Pat. No. 2,327,053 teaches the use of metal halides such as stannic halides, antimony pentahalides, aluminum halides, zinc halides and ferric halides.

A problem associated with these reactions, and in particular the use of alkali or alkaline earth metal alkoxide catalysts, is that the propylene glycol monoalkyl ether product is contaminated with various carbonyl impurities (such as formaldehyde, acetaldehyde, propionaldehyde, acetone, methoxy acetone, and methoxy butenone) that lead to high UV absorption. For particular applications, it may be necessary to limit the amount of carbonyl impurities and thus lower the UV absorbance of the propylene glycol monoalkyl ether product.

In sum, new processes to produce propylene glycol monoalkyl ethers are needed. Particularly useful processes will decrease the amount of carbonyl impurities and thus improve the UV absorbance and color of the propylene glycol monoalkyl ether product. We have discovered an effective, convenient process that produces propylene glycol monoalkyl ether having low UV absorbance.

SUMMARY OF THE INVENTION

The invention is a process which comprises: (a) reacting propylene oxide and an alcohol in the presence of an alkali or alkaline earth metal alkoxide catalyst to produce an alkoxylation mixture comprising propylene glycol monoalkyl ether; (b) distilling the alkoxylation mixture to produce a first overhead stream comprising propylene oxide and the alcohol and a first bottoms stream comprising propylene glycol monoalkyl ether; and (c) distilling the first bottoms stream to produce purified propylene glycol monoalkyl ether as a second overhead stream, wherein the reaction and/or one or more of the distillation steps occur in the presence of alkali metal borohydride. The process surprisingly reduces the carbonyl impurity level and UV absorbance in the propylene glycol monoalkyl ether.

DETAILED DESCRIPTION OF THE INVENTION

The process of the invention comprises first reacting a reaction mixture comprising propylene oxide and an alcohol in the presence of an alkali or alkaline earth metal alkoxide to produce an alkoxylation mixture comprising a propylene glycol monoalkyl ether. In this reaction, two propylene glycol monoalkyl ether isomers, 1-alkoxy-2-propanol and 2-alkoxy-1-propanol, may be produced. For instance the reaction of propylene oxide and methanol produces both 1-methoxy-2-propanol (known as "PM-1") and 2-methoxy-1-propanol ("PM-2"). PM-1, the major product from methanol propoxylation, is the isomer sold commercially.

The process to produce propylene glycol monoalkyl ethers is well known and propylene glycol monoalkyl ethers are commercially available products. Commercial products include Lyondell Chemical Company's ARCOSOLV® propylene glycol ethers, such as ARCOSOLV PM (propylene glycol monomethyl ether), ARCOSOLV PNB (propylene glycol normal butyl ether), ARCOSOLV PTB (propylene glycol tertiary butyl ether), and ARCOSOLV PNP (propylene glycol normal propyl ether).

The reaction mixture comprises propylene oxide and an alcohol. The alcohol used for the reaction is suitably an aliphatic, cycloaliphatic or an aromatic alcohol and may have one, two, or more hydroxyl groups. Preferably, the alcohol has only one hydroxyl group. The alcohol may be primary, secondary or tertiary in structure, and may be saturated or unsaturated as well as substituted with various substituents. Most preferably, the alcohol is a $C_1$-$C_4$ alcohol, particularly, methanol, ethanol, 1-propanol, 2-propanol, 1-butanol, and tert-butanol.

The relative amounts of propylene oxide and alcohol that make up the reaction mixture can vary over a fairly wide range. Usually, however, it is preferred to use at least one mole of alcohol for every propylene oxide equivalent. For example, when methanol reacts with propylene oxide to produce propylene glycol monomethyl ether, it is preferred to use about 2 moles of methanol per mole of propylene oxide. Preferably, the molar ratio of alcohol to propylene oxide is at least 1.1:1 and is more preferably in the range from 1.5:1 to 5:1.

Although not necessary for the reaction, the reaction mixture may also include a solvent. Suitable solvents include $C_5$-$C_{20}$ aliphatic hydrocarbons such as hexane, $C_6$-$C_{20}$ aromatic hydrocarbons such as toluene, nitriles such as acetonitrile, and ethers such as methyl t-butyl ether.

The reaction of propylene oxide with an alcohol is performed in the presence of an alkali or alkaline earth metal alkoxide catalyst. Although any alkali or alkaline earth metal alkoxide may be used (lithium, sodium, potassium, rubidium, cesium, magnesium, calcium, strontium, or barium alkoxides), alkali metal alkoxides are preferred. Potassium alkoxides and sodium alkoxides are particularly preferred. Preferred sodium alkoxides include sodium methoxide, ethoxide, n-propoxide, and n-butoxide, and t-butoxide. Preferred potassium alkoxides include potassium methoxide, ethoxide, n-propoxide, n-butoxide, and t-butoxide. Preferably, the alkoxide corresponds to the alcohol used in the reaction, that is, if the alcohol is methanol then the alkoxide is a methoxide such as sodium methoxide or potassium methoxide.

The reaction of propylene oxide and alcohol to form propylene glycol monoalkyl ether is preferably carried out at a temperature in the range of from about 50° C. to about 250° C., more preferably from about 100° C. to about 180° C. The reaction between propylene oxide and the alcohol is exothermic, so it may be desirable to apply cooling to the reaction mixture in order to control the reaction temperature. The reaction is preferably carried out at atmospheric pressure or at higher pressure up to about 3000 psig (20,786 MPa).

The reaction step of the invention includes batch, semi-batch, and continuous processes. In a typical batch reaction, the reactants (except for the catalyst) are charged to a reactor, catalyst is introduced, and the mixture is heated to the desired reaction temperature to form an alkoxylation mixture comprising propylene glycol monoalkyl ether. In a typical continuous reaction, streams of the propylene oxide, alcohol, any recycle streams, and alkali or alkaline earth metal alkoxide catalyst are fed continuously into a heated reaction zone to form an alkoxylation mixture comprising propylene glycol monoalkyl ether which is continuously withdrawn from the reactor.

Following reaction, the alkoxylation mixture is subjected to distillation in order to produce a propylene glycol monoalkyl ether product. The distillation steps include first distilling the alkoxylation mixture to produce a first overhead stream comprising propylene oxide and alcohol and a first bottoms stream comprising propylene glycol monoalkyl ether; and then distilling the first bottoms stream to produce purified propylene glycol monoalkyl ether as a second overhead stream.

The first distillation step, distilling the alkoxylation mixture, may be operated at any temperature and pressure which will afford a first distillation bottoms stream that contains a higher purity of propylene glycol monoalkyl ether than was contained in the alkoxylation mixture from the reaction. Prior to distillation, the alkoxylation mixture may be sent to a storage unit and/or a finishing drum in order to remove lights from the alkoxylation mixture, however such a storage unit or finishing drum is not necessary for the process of the invention. If the alkoxylation mixture is sent to a finishing drum, the system pressure in the finishing drum is reduced such that a significant amount of unreacted propylene oxide is flashed and vented from the alkoxylation mixture prior to distillation. This flashed propylene oxide may be recycled back to the reaction.

The second distillation step, distilling the first bottoms stream, may be operated at any temperature and pressure which will afford purified propylene glycol monoalkyl ether as the second overhead stream. The purified propylene glycol monoalkyl ether may be a mixture of 1-alkoxy-2-propanol and 2-alkoxy-1-propanol. The purified propylene glycol monoalkyl ether may also be purified 1-alkoxy-2-propanol, wherein any 2-alkoxy-1-propanol produced is separated in the second bottoms stream.

In general, the distillation towers (also referred to as columns) may be of conventional design. The towers are preferentially packed with conventional packing. The temperature and pressure in the towers may be adjusted depending on the type of propylene glycol monoalkyl ether produced.

The first distillation tower is used in order to remove alcohol and propylene oxide as an overhead stream and concentrate propylene glycol monoalkyl ether in the bottoms stream. Preferably, the first distillation tower is operated at a temperature of from about 50° C. to about 200° C. and a pressure of from about 1 psig (108 MPa) to about 150 psig (1136 MPa).

The overhead from the first distillation tower (containing unreacted alcohol and propylene oxide) is preferentially recycled to the reaction step for further reaction. The first distillation bottoms, comprising propylene glycol monoalkyl ether, exits the first tower and is transferred to the second distillation tower for further purification of the propylene glycol monoalkyl ether.

In the second distillation tower, the first distillation bottoms stream is distilled. The overhead stream from the second distillation tower comprises high purity propylene glycol monoalkyl ether. The second distillation bottoms stream, comprising heavier byproducts (such as dipropylene glycol ethers and tripropylene glycol ethers), and optionally 2-alkoxy-1-propanol where 1-alkoxy-2-propanol is purified in the overhead stream, may be recycled back to the reactor or purified further to produce other products. In general, the second distillation tower is operated at a temperature of from about 100° to about 200° C. and a pressure of from about 1 mm Hg (0.133 MPa) to about 760 mm Hg (101.3 MPa).

The purity of the propylene glycol monoalkyl ether stream exiting as an overhead stream from the second distillation column is usually in the range from about 99 to about 99.95 percent.

Without the addition of an alkali metal borohydride to the reaction and/or distillation steps, the propylene glycol monoalkyl ether product typically contains by weight greater than 50 ppm of various carbonyl impurities and gives a UV absorbance (at 245 nm) of greater than 1. Typically, the propylene glycol monoalkyl ether produced with no alkali metal borohydride comprises by weight about 50 to 2,000 ppm of various carbonyl impurities, usually about 50 to 1,000 ppm.

Thus, the process of the invention requires that the reaction and/or one or more of the distillation steps occur in the presence of an alkali metal borohydride. The presence of alkali metal borohydride surprisingly reduces the carbonyl concentration and UV absorption in the propylene glycol monoalkyl ether product. Although any alkali metal borohydride may be used (lithium, sodium, potassium, rubidium, and cesium borohydride), sodium and lithium borohydride are preferred, and sodium borohydride is especially preferred.

If an alkali metal borohydride is added to the reaction mixture, the alkali metal borohydride is preferably added to the reaction mixture such that the reaction mixture comprises from about 0.05 to 100 ppm alkali metal borohydride, more preferably from about 0.1 to 50 ppm alkali metal borohydride.

If an alkali metal borohydride is added to the first distillation step, the alkali metal borohydride may be added into the distillation column as a separate stream from the alkoxylation mixture or may be added into the alkoxylation mixture prior to the first distillation step. Preferably, the alkali metal borohydride is added into the alkoxylation mixture prior to the first distillation step. The alkali metal borohydride is preferably added to the alkoxylation mixture such that the alkoxylation mixture comprises from about 0.1 to 1,000 ppm alkali metal borohydride, more preferably from about 1 to 100 ppm alkali metal borohydride.

If an alkali metal borohydride is added to the second distillation step, the alkali metal borohydride may be added into the distillation column as a separate stream from the first bottoms stream or may be added into the first bottoms stream prior to the second distillation step. Preferably, the alkali metal borohydride is added into the first bottoms stream prior to the second distillation step. The alkali metal borohydride is preferably added to the first bottoms stream such that the first bottoms stream comprises from about 1 to 10,000 ppm alkali metal borohydride, more preferably from about 1 to 100 ppm alkali metal borohydride.

Although an alkali metal borohydride may be added to the reaction step and both distillation steps, it is preferable to add alkali metal borohydride to the first and/or the second distillation step. It is especially preferred to add the alkali metal borohydride to the first distillation step.

Following the process of the invention, a purified propylene glycol monoalkyl ether product having a decreased carbonyl impurities content is produced. Preferably, the purified propylene glycol monoalkyl ether product has a UV absorbance, at 245 nm, of 1 or less.

The following examples merely illustrate the invention. Those skilled in the art will recognize many variations that are within the spirit of the invention and scope of the claims.

EXAMPLE 1

Reaction Runs

Comparison Run 1A: Methanol (132 g), propylene oxide (110 g), and a 2-methoxy-1-propanol recycle mixture (60 g) are added to a stainless steel reactor and the temperature of the reaction mixture is raised to 130° C. A potassium methoxide catalyst mixture (1.27 g, of 25 wt. % $KOCH_3$ in methanol) is added to the reaction mixture and stirred. Samples are taken from the reaction mixture periodically (at 1 h and 10 min and at 2 hr and 10 min after catalyst addition) and analyzed for carbonyl content and UV absorbance. Results are shown in Table 1.

Run 1B: Run 1B is run according to the procedure of Comparison Run 1A with the exception that $NaBH_4$ is added to the reaction mixture with the methanol, resulting in a 0.3 ppm $NaBH_4$ concentration in the reaction mixture. Results are shown in Table 1.

The results show that a small amount of sodium borohydride in the reaction mixture leads to a reduced amount of carbonyl impurities and reduced UV absorbance.

EXAMPLE 2

Batch Distillation Runs

Comparison Run 2A: A 1-methoxy-2-propanol reaction solution (1198.3 g, containing 778.19 g PM-1) is distilled under vacuum using an 8 mm I.D. spinning band batch distillation column (B/R Instrument Corporation, Easton Md.). The condenser pressure is controlled at 368 mm Hg (49 MPa) and the reflux ratio is set at 50 to 1. This results in a boiling temperature of 105° C. in the distillation reboiler pot. Samples of the overhead, purified PM-1 are taken in 20 mL increments and analyzed for carbonyl content and UV absorbance (at 245 nm). Results are shown in Table 2.

Run 2B: Run 2B is run according to the procedure of Comparison Run 2A with the exception that 200 ppm $NaBH_4$ (0.24 g) is added to the 1-methoxy-2-propanol solution (1200 g, containing 779.29 g PM-1). Results are shown in Table 2.

The results show that the addition of sodium borohydride into the batch distillation pot leads to a reduced amount of carbonyl impurities and reduced UV absorbance for the first 40 mL of PM-1 collected overhead, until the sodium borohydride in the pot was depleted after about 7 hours at 105° C.

EXAMPLE 3

Continuous Distillation Runs

Comparison Run 3A: A 1-methoxy-2-propanol reaction solution, containing 65 wt. % PM-1, is purified by continuous distillation under vacuum using a distillation column (1 in. I.D.×4 ft) containing PRO-PAK® packing. The 1-methoxy-2-propanol reaction solution is fed into the distillation column at 18 inches from the bottom of the column and the temperature at the feeding tray is maintained at 118-119° C. during the distillation procedure. Feed rate is adjusted to reach a desired liquid residence time. The reboiler liquid volume is controlled at 220 mL and pot temperature is maintained at 121-122° C. The reflux ratio is controlled at 5 to 1. Purified PM-1 product is withdrawn continuously overhead. PM-1 product samples are analyzed for carbonyl content and UV absorbance (at 245 nm). Results are shown in Table 3.

Run 3B: Run 3B is run according to the procedure of Comparison Run 3A with the exception that 42 ppm $NaBH_4$ is added to the 1-methoxy-2-propanol reaction solution. Results are shown in Table 3.

The results show that the addition of sodium borohydride into the continuous distillation reduces both carbonyl impurities and UV absorbance for the PM-1 product collected overhead.

TABLE 1

Reaction Run Data

| Run # | Sample Time | Carbonyl Amount (ppm) | UV, abs. |
|---|---|---|---|
| 1A* | 1:10 | 28 | 1.05 |
| 1B | 1:10 | 26 | 0.87 |
| 1A* | 2:10 | 36 | 1.64 |
| 1B | 2:10 | 30 | 1.3 |

*Comparative Example

TABLE 2

Distillation Run Data

| Run # | PM-1 Collected Overhead (mL) | Carbonyl Amount (ppm) | UV, abs. |
|---|---|---|---|
| 2A* | 20 | 1209 | 3.87 |
| 2B | 20 | 10 | 0.16 |
| 2A* | 40 | 609 | 3.21 |
| 2B | 40 | 8 | 0.15 |
| 2A* | 60 | 351 | 2.66 |
| 2B | 60 | 388 | 0.86 |

*Comparative Example

TABLE 3

Distillation Run Data

| Run # | Residence Time (minute) | Carbonyl Amount (ppm) | UV, abs. |
|---|---|---|---|
| 3A* | 115 | 58 | 0.96 |
| 3B | 119 | 6 | 0.16 |
| 3A* | 59 | 54 | 0.96 |
| 3B | 68 | 9 | 0.16 |
| 3A* | 42 | 76 | 1.01 |
| 3B | 46 | 21 | 0.21 |

*Comparative Example

We claim:

1. A process for producing a propylene glycol monoalkyl ether which comprises:
   (a) reacting propylene oxide and an alcohol in the presence of an alkali or alkaline earth metal alkoxide catalyst to produce an alkoxylation mixture comprising propylene glycol monoalkyl ether and a component having a carbonyl functional group;
   (b) distilling the alkoxylation mixture at a temperature of from about 50° C. to about 200° C. and a pressure of from about 1 psig to about 150 psig to produce a first overhead stream comprising propylene oxide and the alcohol and a first bottoms stream comprising propylene glycol monoalkyl ether; and (c) distilling the first bottoms stream to produce purified propylene glycol monoalkyl ether as a second overhead stream, wherein the reaction and/or one or more of the distillation steps occur in the presence of 0.05 to 1000 ppm, based upon the total weight of the alkoxylation mixture, of an alkali metal borohydride, and wherein the alkali metal borohydride reduces the concentration of the component having a carbonyl functional group.

2. The process of claim 1 wherein the alcohol is a $C_1$-$C_4$ alcohol.

3. The process of claim 1 wherein the alcohol is selected from the group consisting of methanol, 1-propanol, 1-butanol, and tert-butanol.

4. The process of claim 1 wherein the alkali or alkaline earth metal alkoxide catalyst is an alkali metal alkoxide.

5. The process of claim 4 wherein the alkali metal alkoxide catalyst is a potassium alkoxide or a sodium alkoxide.

6. The process of claim 5 wherein the potassium alkoxide is selected from the group consisting of potassium methoxide, potassium n-propoxide, potassium n-butoxide, and potassium t-butoxide.

7. The process of claim 5 wherein the sodium alkoxide is selected from the group consisting of sodium methoxide, sodium n-propoxide, sodium n-butoxide, and sodium t-butoxide.

8. The process of claim 1 wherein the alkali metal borohydride is sodium borohydride.

9. The process of claim 1 wherein the first overhead stream is recycled back to the reaction step (a).

10. The process of claim 1 wherein the propylene glycol monoalkyl ether is propylene glycol monomethyl ether.

11. The process of claim 1 wherein the alkali metal borohydride is added into the alkoxylation mixture prior to distillation step (b).

12. The process of claim 1 wherein the alkali metal borohydride is added into the first bottoms stream prior to distillation step (c).

13. The process of claim 1 wherein the purified propylene glycol monoalkyl ether has a UV absorbance, at 245 nm, of 1 or less.

14. A process for producing a propylene glycol monomethyl ether which comprises:

(a) reacting propylene oxide and methanol in the presence of an alkali metal methoxide catalyst to produce an alkoxylation mixture comprising propylene glycol monomethyl ether and a component having a carbonyl functional group;

(b) distilling the alkoxylation mixture at a temperature of from about 50° C. to about 200° C. and a pressure of from about 1 psiq to about 150 psiq to produce a first overhead stream comprising propylene oxide and methanol and a first bottoms stream comprising propylene glycol monomethyl ether; and (c) distilling the first bottoms stream to produce purified propylene glycol monomethyl ether as a second overhead stream, wherein the reaction and/or one or more of the distillation steps occur in the presence of 0.05 to 1000 ppm, based upon the total weight of the alkoxylation mixture, of sodium borohydride, and wherein the sodium borohydride reduces the concentration of the component having a carbonyl functional group.

15. The process of claim 14 wherein the alkali metal methoxide catalyst is potassium methoxide.

16. The process of claim 14 wherein the alkali metal methoxide catalyst is sodium methoxide.

17. The process of claim 14 wherein the first overhead stream is recycled back to the reaction step (a).

18. The process of claim 14 wherein the sodium borohydride is added into the alkoxylation mixture prior to distillation step (b).

19. The process of claim 14 wherein the sodium borohydride is added into the first bottoms stream prior to distillation step (c).

20. The process of claim 14 wherein the purified propylene glycol monomethyl ether has a UV absorbance, at 245 nm, of 1 or less.

* * * * *